(12) United States Patent
Printy et al.

(10) Patent No.: US 7,319,530 B1
(45) Date of Patent: Jan. 15, 2008

(54) SYSTEM AND METHOD FOR MEASURING GERMANIUM CONCENTRATION FOR MANUFACTURING CONTROL OF BICMOS FILMS

(75) Inventors: Craig Printy, Buxton, ME (US); Thanas Budri, Portland, ME (US)

(73) Assignee: National Semiconductor Corporation, Santa Clara, CA (US)

( * ) Notice: Subject to any disclaimer, the term of this patent is extended or adjusted under 35 U.S.C. 154(b) by 309 days.

(21) Appl. No.: 10/811,738

(22) Filed: Mar. 29, 2004

(51) Int. Cl.
*G01B 11/28* (2006.01)
*H01L 21/66* (2006.01)

(52) U.S. Cl. .............. 356/630; 438/8; 438/14

(58) Field of Classification Search ........... 356/630, 356/364–369; 250/492.2, 225; 438/8, 14, 438/17; 702/172; 324/767
See application file for complete search history.

(56) References Cited

U.S. PATENT DOCUMENTS

| | | | | |
|---|---|---|---|---|
| 5,256,550 A * | 10/1993 | Laderman et al. | ........ | 438/509 |
| 5,298,860 A * | 3/1994 | Kato | ........ | 324/767 |
| 5,476,813 A * | 12/1995 | Naruse | ........ | 438/311 |
| 5,818,596 A * | 10/1998 | Imai et al. | ........ | 356/630 |
| 5,863,807 A * | 1/1999 | Jang et al. | ........ | 438/14 |
| 5,982,496 A * | 11/1999 | Ziger | ........ | 356/630 |
| 6,010,914 A * | 1/2000 | Shishiguchi | ........ | 438/14 |
| 6,277,657 B1 * | 8/2001 | Nozawa et al. | ........ | 438/8 |
| 6,278,519 B1 * | 8/2001 | Rosencwaig et al. | ........ | 356/369 |
| 6,331,890 B1 * | 12/2001 | Marumo et al. | ........ | 356/369 |
| 6,519,045 B2 * | 2/2003 | Kwon | ........ | 356/630 |
| 6,521,041 B2 * | 2/2003 | Wu et al. | ........ | 117/94 |
| 6,573,126 B2 * | 6/2003 | Cheng et al. | ........ | 438/149 |
| 6,639,228 B2 * | 10/2003 | Yen | ........ | 250/492.2 |
| 6,731,386 B2 * | 5/2004 | Dautartas et al. | ........ | 356/369 |
| 6,759,255 B2 * | 7/2004 | Xu et al. | ........ | 438/14 |
| 6,895,360 B2 * | 5/2005 | Liu et al. | ........ | 702/172 |

FOREIGN PATENT DOCUMENTS

JP      06275689 A   *   9/1994

* cited by examiner

*Primary Examiner*—Sang H. Nguyen

(57) ABSTRACT

A system and method is disclosed for measuring a germanium concentration in a semiconductor wafer for manufacturing control of BiCMOS films. Germanium is deposited over a silicon substrate layer to form a silicon germanium film. Then a rapid thermal oxidation (RTO) procedure is performed to create a layer of thermal oxide over the silicon germanium film. The thickness of the layer of thermal oxide is measured in real time using an interferometer, an ellipsometer, or a spectroscopic ellipsometer. The measured thickness of the layer of thermal oxide is correlated to a germanium concentration of the silicon germanium film using an approximately linear correlation. The correlation enables a value of the germanium concentration in the silicon germanium film to be provided in real time.

20 Claims, 6 Drawing Sheets

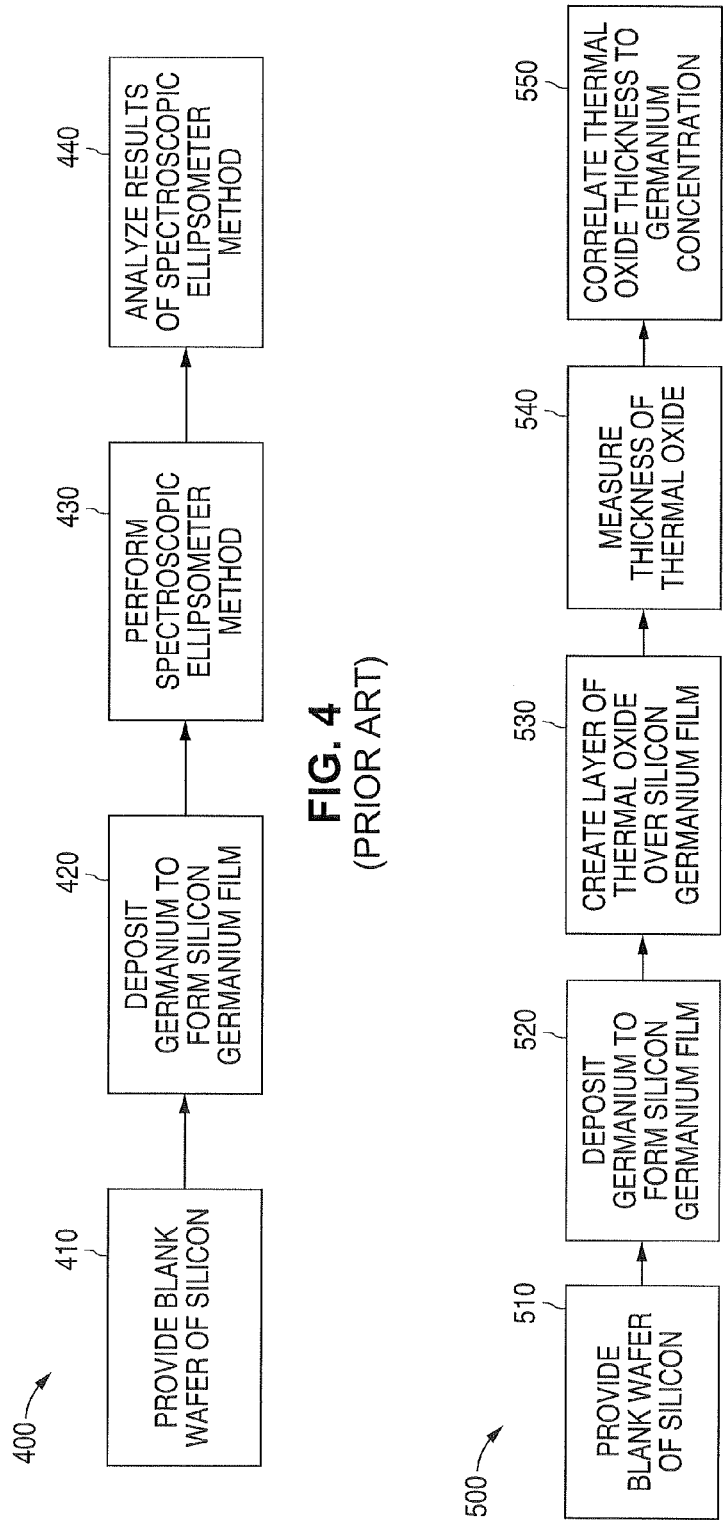

SYSTEM AND METHOD FOR MEASURING GERMANIUM CONCENTRATION FOR MANUFACTURING CONTROL OF BICMOS FILMS

TECHNICAL FIELD OF THE INVENTION

The present invention is generally directed to manufacturing technology for semiconductor devices and, in particular, to a system and method for measuring a germanium concentration in a semiconductor wafer for manufacturing control of BiCMOS films.

BACKGROUND OF THE INVENTION

The overwhelming majority of microelectronic devices in current use are based on silicon technology. However, more and more microelectronic devices are being based on silicon germanium (SiGe) technology. Silicon germanium technology has numerous advantages. Silicon germanium technology is capable of providing higher operating speeds, lower levels of noise, lower levels of power consumption, and higher levels of integration. Silicon germanium technology is currently being employed in wireless radio frequency (RF) integrated circuits.

In a silicon germanium (SiGe) integrated circuit the combination of silicon and germanium improves the electrical properties of the integrated circuit. For example, the addition of germanium to a silicon bipolar transistor improves the operating frequency, current, noise, and power capabilities of the transistor.

Silicon germanium (SiGe) technology is also being employed in the manufacture of BiCMOS films. BiCMOS is an integrated circuit technology that incorporates bipolar (Bi) semiconductor devices and complementary metal oxide (CMOS) semiconductor devices on the same integrated circuit die.

During the manufacture of a BiCMOS film it is important to be able to determine how much germanium (Ge) is present in a silicon germanium film. If too much or too little germanium is used in the silicon germanium film then the film will not have the desired operating characteristics. In order to provide quality control of the manufacturing process it is necessary to measure the germanium concentration during the manufacturing process.

A number of prior art methods exist for measuring the concentration of germanium in a silicon germanium film. A first prior art method involves monitoring the germanium concentration using a secondary ion mass spectrometer (SIMS). A second prior art method involves monitoring the germanium concentration using high resolution X-ray diffraction (HRXDF). A third prior art method involves monitoring the germanium concentration using Raman spectroscopy. A fourth prior art method involves monitoring the germanium concentration using a spectroscopic ellipsometer (SE).

These prior art methods have significant drawbacks. The prior art methods tend to be relatively expensive and must be performed by a highly qualified engineer. Some of the prior art methods require considerable time to perform. For example, the SIMS method can take up to three (3) days to perform. In addition, the prior art methods usually require the services of an external analytical laboratory in order to obtain the desired germanium concentration measurements. The prior art methods can not detect deviations in the germanium concentration in a real time manner or provide a measurement of the germanium concentration in a silicon germanium film in a real time manner.

Therefore, there is a need in the art for a system and method for measuring a germanium concentration in a semiconductor wafer for manufacturing control of a BiCMOS film. There is a need in the art for a system and method for making inexpensive real time measurements of germanium concentration in order to detect process deviations of a germanium concentration in a real time manner.

SUMMARY OF THE INVENTION

To address the above-discussed deficiencies of the prior art, it is a primary object of the present invention to provide a system and method for measuring a germanium concentration in a silicon germanium film in a semiconductor wafer.

In one advantageous embodiment of the present invention a silicon germanium film is constructed on a silicon substrate in the following manner. First an underlying silicon substrate layer is provided. Then germanium is deposited to form a silicon germanium film on the top of the silicon substrate. Then a rapid thermal oxidation (RTO) procedure is performed to create a layer of thermal oxide over the silicon germanium film. The thickness of the layer of thermal oxide is then measured in real time using either an interferometer, or an ellipsometer, or a spectroscopic ellipsometer.

The inventors of the present invention have discovered an approximately linear correlation between the germanium concentration in a silicon germanium film and a thickness of a layer of thermal oxide grown over the silicon germanium film. The measured thickness of the layer of thermal oxide is correlated to a germanium concentration of the silicon germanium film using the approximately linear correlation. The correlation enables a value of the germanium concentration in the silicon germanium film to be provided in a real time manner.

It is an object of the present invention to provide a system and method for measuring a germanium concentration in a semiconductor wafer for manufacturing control of a BiCMOS film.

It is also an object of the present invention to provide a system and method for making inexpensive real time measurements of germanium concentration in order to detect process deviations of a germanium concentration in a real time manner.

It is yet another object of the present invention to provide an approximately linear correlation between a germanium concentration in a silicon germanium film and a thickness of a layer of thermal oxide grown over the silicon germanium film.

It is still another object of the present invention to provide a system and method for correlating a measured thickness of a layer of thermal oxide to a germanium concentration of a silicon germanium film using an approximately linear correlation.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description of the Invention below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior uses, as well as future uses, of such defined words and phrases.

BRIEF DESCRIPTION OF THE DRAWINGS

For a more complete understanding of the present invention and its advantages, reference is now made to the following description taken in conjunction with the accompanying drawings, in which like reference numerals represent like parts:

FIG. 4 illustrates a fourth prior art method for measuring a germanium concentration in a silicon germanium film;

FIG. 5 illustrates a method for measuring a germanium concentration in a silicon germanium film in accordance with the principles of the present invention;

DETAILED DESCRIPTION OF THE INVENTION

Figure 1:
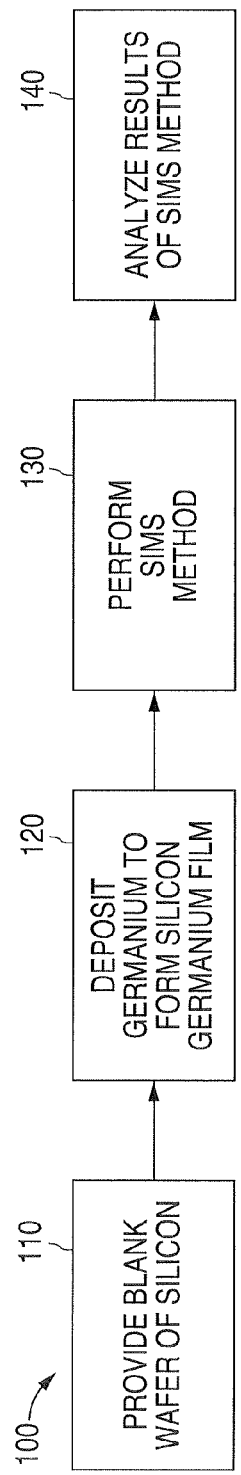
FIG. 1 illustrates a first prior art method for measuring a germanium concentration in a silicon germanium film.

FIGS. 1 through 13, discussed below, and the various embodiments used to describe the principles of the present invention in this patent document are by way of illustration only and should not be construed in any way to limit the scope of the invention. Those skilled in the art will understand that the principles of the present invention may be implemented in any type of suitably arranged semiconductor device.

To simplify the drawings the reference numerals from previous drawings may sometimes not be repeated for structures that have already been identified.

FIG. 1 illustrates a prior art method 100 for measuring the concentration of germanium in a silicon germanium film. The germanium concentration is measured using a secondary ion mass spectrometer (SIMS). In the first step of the method a blank wafer of silicon is provided (step 110). Then germanium is deposited on the silicon to form a silicon germanium film (step 120). The germanium may be deposited by a prior art method that exposes the silicon blank wafer to a gas comprising silane gas ($SiH_4$) and germane gas ($GeH_4$) in a hydrogen gas ($H_2$) carrier.

Then the germanium concentration in the silicon germanium film is measured using a secondary ion mass spectrometer (SIMS) (step 130). Then the results of the SIMS method are analyzed to determine the percentage of germanium in the silicon germanium film (step 140).

Although the SIMS method is thorough and accurate, the SIMS method has significant drawbacks. The SIMS method is destructive and relatively expensive. The SIMS method must be performed by an engineer. The SIMS method can take up to three (3) days to perform. An engineer is required to interpret the SIMS results. The engineer may take up to an hour to analyze the SIMS results. The SIMS method usually requires the services of an external analytical laboratory in order to obtain the desired germanium concentration measurements. Therefore, the SIMS method cannot detect deviations in the germanium concentration in a real time manner or provide a measurement of the germanium concentration in a real time manner.

Figure 2:
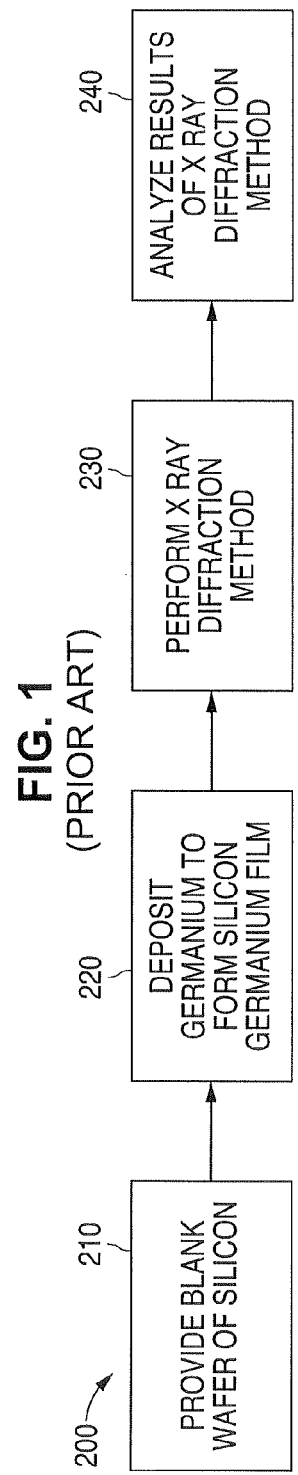
FIG. 2 illustrates a second prior art method for measuring a germanium concentration in a silicon germanium film.

FIG. 2 illustrates a prior art method 200 for measuring the concentration of germanium in a silicon germanium film. The germanium concentration is measured using high resolution X-ray diffraction (HRXDF). In the first step of the method a blank wafer of silicon is provided (step 210). Then germanium is deposited on the silicon to form a silicon germanium film (step 220). The germanium may be deposited by a prior art method that exposes the silicon blank wafer to a gas comprising silane gas ($SiH_4$) and germane gas ($GeH_4$) in a hydrogen gas ($H_2$) carrier.

Then the germanium concentration in the silicon germanium film is measured using high resolution X-ray diffraction (HRXDF) (step 230). Then the results of the X-ray diffraction are analyzed to determine the percentage of germanium in the silicon germanium film (step 240).

The X-ray diffraction method is capable of measuring the germanium layer thickness and concentration in a silicon germanium film. However, the X-ray diffraction method is relatively expensive and time consuming. The X-ray diffraction method must be performed by an engineer. The X-ray diffraction measurement may take an hour to perform. An engineer is required to interpret the X-ray diffraction results. The engineer may take up to an hour to analyze the X-ray diffraction results. Therefore, the X-ray diffraction method cannot detect deviations in the germanium concentration in a real time manner or provide a measurement of the germanium concentration in a real time manner.

Figure 3:
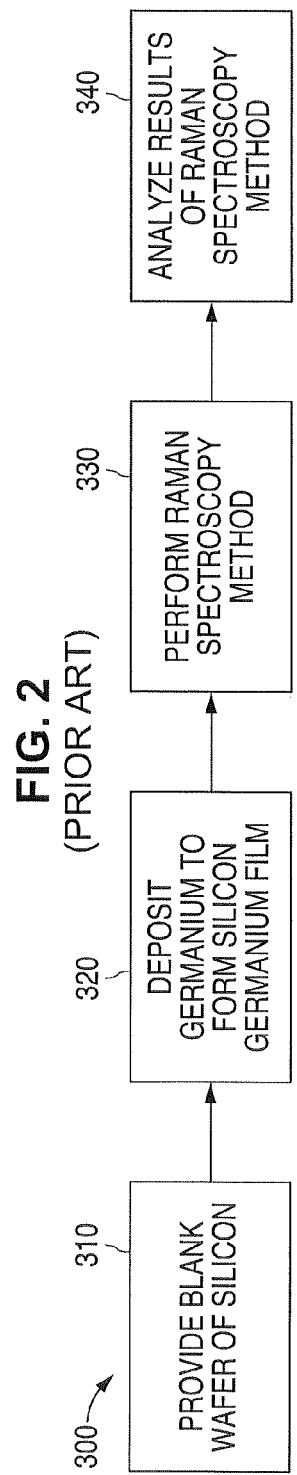
FIG. 3 illustrates a third prior art method for measuring a germanium concentration in a silicon germanium film.

FIG. 3 illustrates a prior art method 300 for measuring the concentration of germanium in a silicon germanium film. The germanium concentration is measured using Raman spectroscopy. In the first step of the method a blank wafer of silicon is provided (step 310). Then germanium is deposited on the silicon to form a silicon germanium film (step 320). The germanium may be deposited by a prior art method that exposes the silicon blank wafer to a gas comprising silane gas ($SiH_4$) and germane gas ($GeH_4$) in a hydrogen gas ($H_2$) carrier.

Then the germanium concentration in the silicon germanium film is measured using Raman spectroscopy (step 330). Then the results of the Raman spectroscopy method are analyzed to determine the percentage of germanium in the silicon germanium film (step 340).

The Raman spectroscopy method is capable of measuring the germanium layer thickness and concentration in a silicon germanium film. However, the Raman spectroscopy method is relatively expensive and time consuming. The Raman spectroscopy method must be performed by an engineer. The Raman spectroscopy measurement may take an hour to perform. An engineer is required to interpret the Raman spectroscopy results. The engineer may take up to an hour to analyze the Raman spectroscopy results. Therefore, the Raman spectroscopy method also cannot detect deviations in the germanium concentration in a real time manner or provide a measurement of the germanium concentration in a real time manner.

FIG. 4 illustrates a prior art method 400 for measuring the concentration of germanium in a silicon germanium film. The germanium concentration is measured using a spectroscopic ellipsometer. In the first step of the method a blank wafer of silicon is provided (step 410). Then germanium is deposited on the silicon to form a silicon germanium film (step 420). The germanium may be deposited by a prior art method that exposes the silicon blank wafer to a gas comprising silane gas ($SiH_4$) and germane gas ($GeH_4$) in a hydrogen gas ($H_2$) carrier.

Then the germanium concentration in the silicon germanium film is measured using a spectroscopic ellipsometer (step 430). Then the results of the spectroscopic ellipsometer method are analyzed to determine the percentage of germanium in the silicon germanium film (step 440).

The spectroscopic ellipsometer method is capable of measuring the germanium layer thickness and concentration in a silicon germanium film. However, the spectroscopic ellipsometer method is relatively expensive and time consuming. The spectroscopic ellipsometer method for measuring a thickness of a silicon germanium film utilizes a harmonic oscillator model. The method based on the harmonic oscillator model must be performed by an engineer.

The harmonic oscillator model is based on complex equations that predict the interaction of light with a material. The harmonic oscillator model comprises one or more harmonic oscillators, each of which has its own characteristic resonant and damping energy. The harmonic oscillator method requires the generation of a "spectra" from the sample of material. A "spectra" is a curve that shows the effect of the material on each wavelength that is used by the spectroscopic ellipsometer. An engineer must modify the resonant, damping energies (and other model parameters) until the harmonic oscillator model produces a spectra that matches the measured spectra. The harmonic oscillator values are then compared to a calibration curve of resonant energy to germanium percentage (Ge %) in order to determine the composition of the material.

The measurement based on the harmonic oscillator method using a spectroscopic ellipsometer may take an hour to perform. An engineer is required to interpret the spectroscopic ellipsometer results. The engineer may take up to an hour to analyze the spectroscopic ellipsometer results. Therefore, the spectroscopic ellipsometer method also cannot detect deviations in the germanium concentration in a real time manner or provide a measurement of the germanium concentration in a real time manner.

FIG. 5 illustrates a method 500 of the present invention for measuring the concentration of germanium in a silicon germanium film. In the first step of method 500 a blank wafer of silicon is provided (step 510). Then germanium is deposited on the silicon to form a silicon germanium film (step 520). The germanium may be deposited by a prior art method that exposes the silicon blank wafer to a gas comprising silane gas ($SiH_4$) and germane gas ($GeH_4$) in a hydrogen gas ($H_2$) carrier.

The silicon germanium film is then subjected to a rapid thermal oxidation (RTO) procedure (or, alternatively, a furnace oxidation procedure) to create a layer of thermal oxide over the silicon germanium film (step 530). Then the thickness of the thermal oxide is measured using an ellipsometer (step 540). Then the percentage of germanium in the silicon germanium film (i.e., the germanium concentration) is obtained from the thickness measurement of the thermal oxide layer (step 550). The steps of the method 500 of the present invention will now be discussed in more detail.

Figure 6:
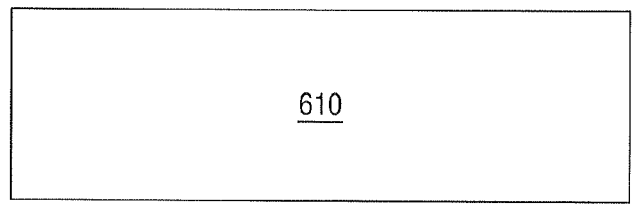
FIGS. 6 through 8 illustrate successive stages in the construction of a silicon germanium film and thermal oxide layer in accordance with the principles of the present invention.
Figure 7:
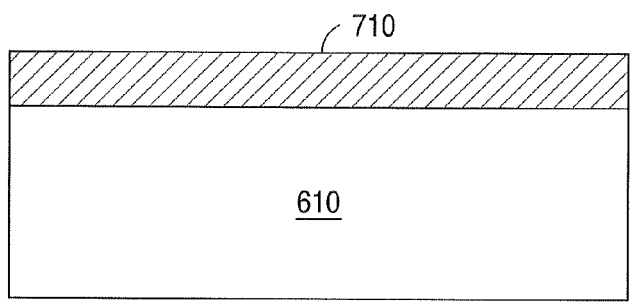
Figure 8:
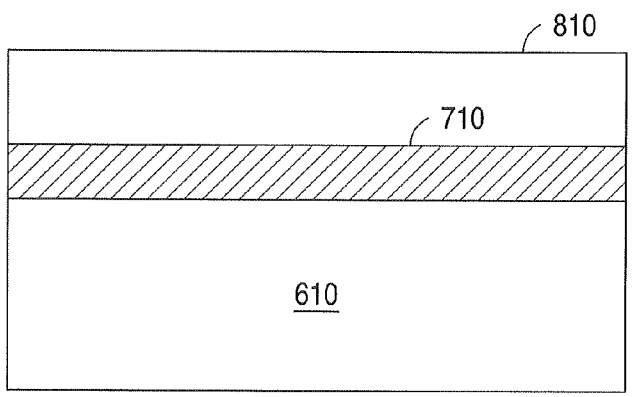

FIGS. 6 through 8 illustrate successive stages in the construction of a silicon germanium film and a thermal oxide layer in accordance with the principles of the present invention. First, as shown in FIG. 6, a blank wafer of silicon 610 is provided. Then, as shown in FIG. 7, germanium is deposited on the blank wafer of silicon 610 to form a silicon germanium film 710. For clarity, the silicon germanium film 710 in FIG. 7 is not drawn to scale. The germanium may be deposited by a prior art method that exposes the blank wafer of silicon 610 to a gas comprising silane gas ($SiH_4$) and germane gas ($GeH_4$) in a hydrogen gas ($H_2$) carrier.

The silicon germanium film 710 is then subjected to a rapid thermal oxidation (RTO) procedure (or, alternatively, a furnace oxidation procedure) to create a layer of thermal oxide 810 over the silicon germanium film 710. The layer of thermal oxide 810 is shown in FIG. 8. For clarity, the silicon germanium film 710 and the layer of thermal oxide 810 in FIG. 8 are not drawn to scale.

Figure 9:
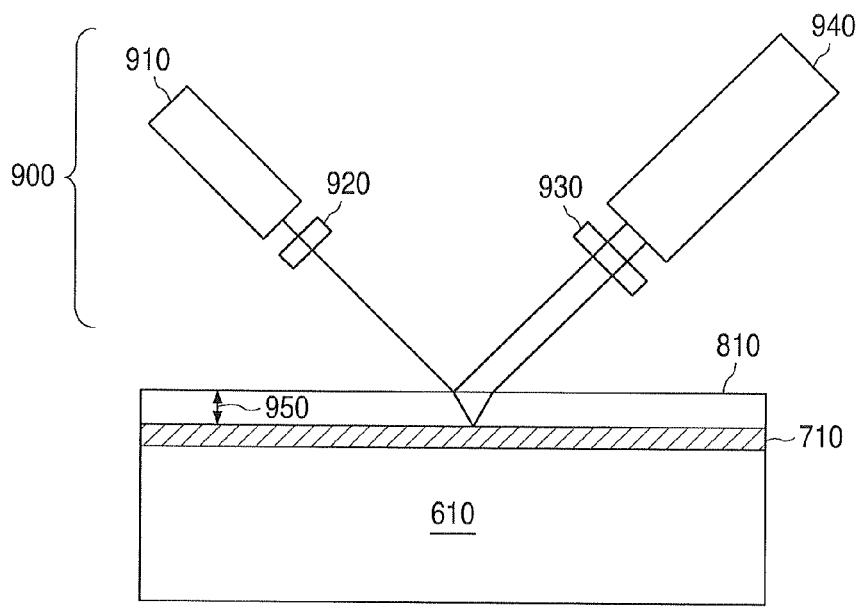
FIG. 9 illustrates an ellipsometer measurement of the thickness of the thermal oxide layer of the present invention.

Then the thickness of the layer of thermal oxide 810 is measured. One advantageous method for measuring the thickness of the layer of thermal oxide 810 uses either an ellipsometer or a spectroscopic ellipsometer. FIG. 9 illustrates an exemplary spectrographic ellipsometer 900. Ellipsometer 900 is capable of measuring the refractive index and the thickness of semi-transparent thin films. In the present invention, because it is the thickness of the layer of thermal oxide 810 that is being measured, it is not necessary to employ the relatively expensive and complex method based on the harmonic oscillator model.

Ellipsometer 900 comprises a laser unit 910, a polarizer unit 920, an analyzer unit 930 and a detector unit 940. The operation of ellipsometer 900 relies on these principles: (1) that the reflection of light at a dielectric interface depends on the polarization of the light, and (2) that the transmission of light through a transparent layer changes the phase of the incoming wave depending on the refractive index of the material. An ellipsometer 900 can be used to measure layers as thin as one nanometer (1.0 nm) and layers that are up to several microns in thickness. A nanometer is equal to one billionth of a meter ($10^{-9}$ m) and a micron is equal to one millionth of a meter ($10^{-6}$ m).

In one advantageous embodiment of ellipsometer 900 the laser unit 910 comprises a 632.8 nanometer helium-neon laser. Polarizer unit 920 of ellipsometer 900 may comprise a polarizer and a quarter wave plate that is capable of providing a state of polarization of the light from laser unit 910. The state of polarization may be varied from (1) linearly polarized light to (2) elliptically polarized light to (3) circularly polarized light by varying the angle of the polarizer.

The beam of light from laser unit 910 passes through polarizer unit 920 and is reflected off the surface of the layer of thermal oxide 810. The reflected beam passes through analyzer unit 930 and detector unit 940. As shown in FIG. 9, a portion of the beam of light from laser unit 910 is refracted through the layer of thermal oxide 810 and reflected from the upper surface of silicon germanium film 710. This refracted and reflected beam exits from the layer of thermal oxide 810 and passes through analyzer unit 930 and detector unit 940. Detector unit 940 is capable of using information concerning the settings of polarizer unit 920 and analyzer unit 930 to determine the thickness 950 of the layer of thermal oxide 810.

Ellipsometer 900 uses a model based on a lookup table for values of index of refraction (n) and wave number (k). A spectra is generated for the layer of thermal oxide 810 on top of the silicon germanium film 710. Ellipsometer 900 automatically adjusts parameters in an Index and Absorption Dispersion Model until the predicted spectra matches the measured spectra. The model parameters are then used to find the correct value of thickness 950 of the layer of thermal oxide 810 in a lookup table. No input is required by the operator to obtain the thickness measurement for the layer of thermal oxide 810.

One major advantage of using ellipsometer 900 is that the thickness measurements of the layer of thermal oxide 810 may be made quickly (i.e., in real time) and inexpensively. For example, the thickness 950 of the layer of thermal oxide 810 may be measured within about five minutes at a cost of about one dollar. In addition, the operator of ellipsometer 900 does not need to be a trained engineer. The rapidity with which the thickness measurements can be made means that ellipsometer 900 may be used to obtain thickness measurements at a plurality of sites on the layer of thermal oxide 810. Unlike the prior art methods, the measurement method of the present invention is capable of making several measurements in a real time manner.

Then the percentage of germanium in the silicon germanium film 710 (i.e., the germanium concentration) is obtained from the thickness measurement 950 of the layer of thermal oxide 810. The inventors of the present invention have discovered an approximately linear correlation between the germanium concentration in the silicon germanium film 710 and the thickness 950 of the layer of thermal oxide 810.

Figure 10:
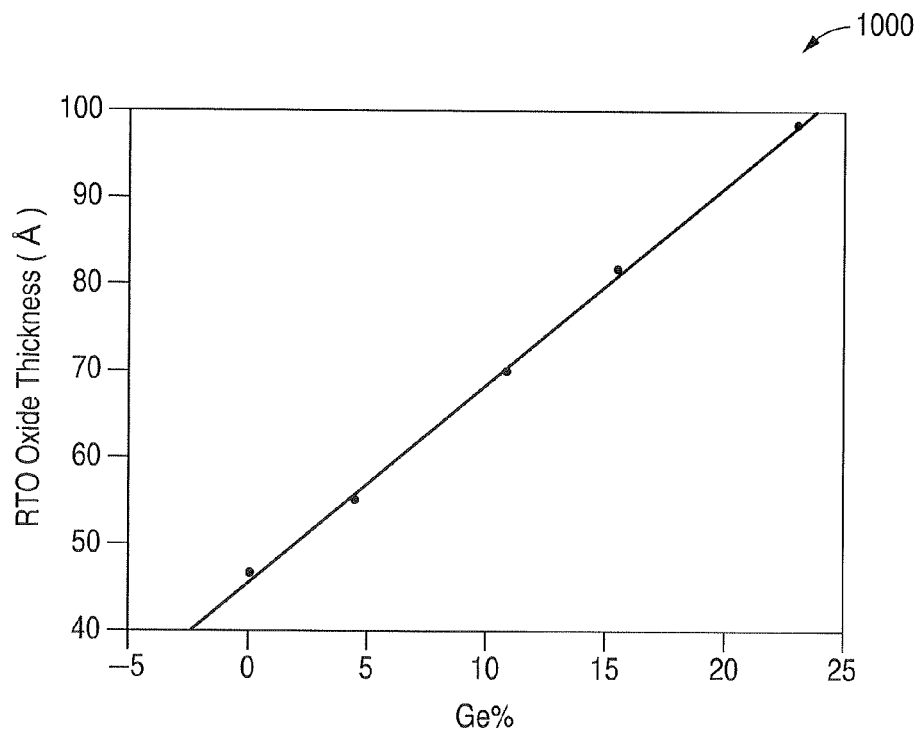
FIG. 10 illustrates a graph of thermal oxide thickness versus germanium concentration showing an approximately linear correlation.

FIG. 10 illustrates a graph 1000 of thermal oxide thickness versus germanium concentration showing an approximately linear correlation. To obtain the information that is graphically shown in FIG. 10 five different silicon germanium layers in five different silicon wafers were manufactured and tested. Each of the five silicon germanium layers was grown with a different germanium concentration. All five of the test wafers were then subjected to a standard rapid thermal oxidation (RTO) procedure. The germanium concentration for each of the test wafers was measured using a secondary ion mass spectrometer (SIMS). The thickness of the layer of thermal oxide for each of the test wafers was measured using a spectroscopic ellipsometer.

The thickness measurement results for the layer of thermal oxide (in units of Ångstroms) were then plotted versus the germanium concentration (in units of percent germanium). The resulting correlation is shown in FIG. 10 in graph 1000. An empirical equation for the best fit line shown in graph 1000 is RTO Oxide Thickness (in Ångstroms) =45.55035+2.2670656 Ge %. A corresponding value of germanium concentration for a measured thickness of thermal oxide may be obtained directly from graph 1000.

Figure 11:
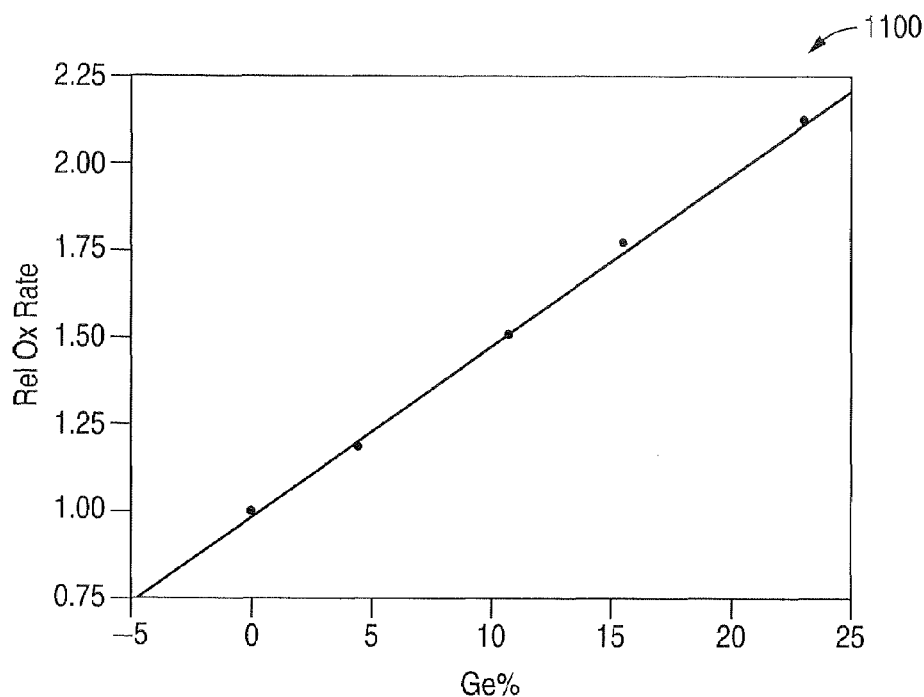
FIG. 11 illustrates a graph of relative oxidation rate versus germanium concentration showing an approximately linear correlation.

FIG. 11 illustrates a graph 1100 of relative oxidation rate versus germanium concentration showing an approximately linear correlation. While graph 1000 relates an actual thickness of a layer of thermal oxide to a corresponding germanium concentration, graph 1100 relates a relative oxidation rate to a corresponding germanium concentration.

For example, consider a procedure in which a silicon wafer with no silicon germanium film and a silicon wafer with a silicon germanium film are each subjected to a rapid thermal oxidation procedure (RTO). The thermal oxide layer on each wafer is then measured. Assume that the thickness of the layer of thermal oxide on the wafer with the silicon germanium film is twice that of the thickness of the layer of thermal oxide on the wafer with no silicon germanium film. This means that the wafer with the silicon germanium film has a relative oxidation rate of two (2.00). From graph 1100 in FIG. 11 it is seen that a relative oxidation rate of two (2.00) means that the wafer with the silicon germanium film has a germanium concentration of approximately twenty one percent (21%).

The values of relative oxidation rate were plotted versus the germanium concentration (in units of percent germanium). The resulting correlation is shown in FIG. 11 in graph 1100. An empirical equation for the best fit line shown in graph 1100 is Relative Oxidation Rate=0.9795774+ 0.0487541 Ge %. A corresponding value of germanium concentration for a measured relative oxidation rate of thermal oxide may be obtained directly from graph 1100.

Figure 12:
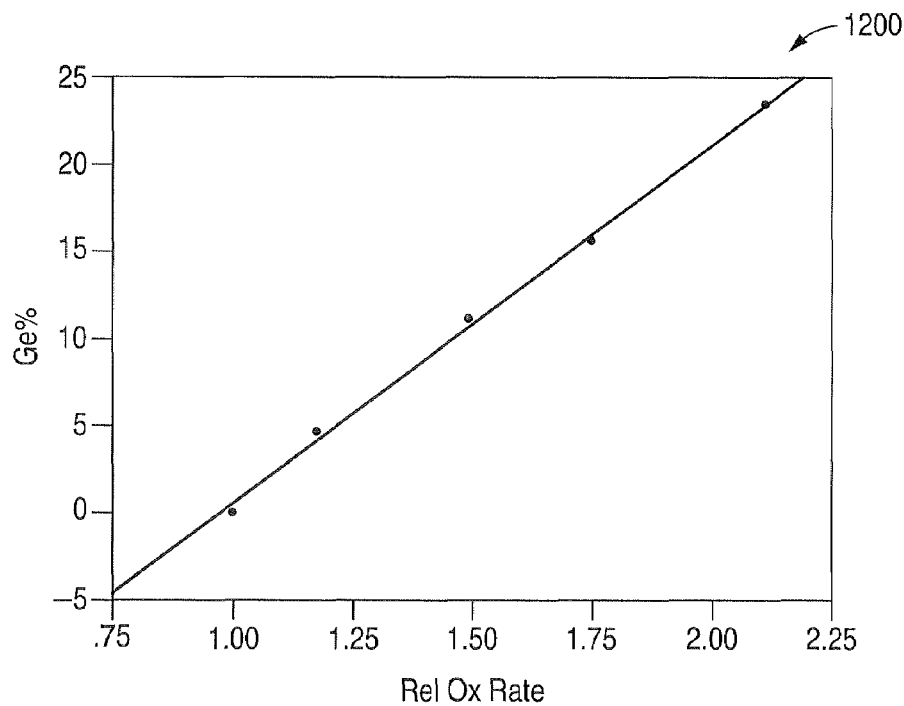
FIG. 12 illustrates a graph of germanium concentration versus relative oxidation rate showing an approximately linear correlation.

FIG. 12 illustrates a graph 1200 of germanium concentration versus relative oxidation rate showing an approximately linear correlation. Graph 1200 of FIG. 12 is a reciprocal version of graph 1100 shown in FIG. 11. An empirical equation for the best fit line shown in graph 1200 is:

Ge %=−20.03043+20.470103 Rel Ox Rate.

Consider the preceding example in which the relative oxidation rate (Rel Ox Rate) was two (2.00). A value of two (2.00) for the relative oxidation rate gives a value of 20.91% (or approximately 21%) for the germanium concentration (Ge %).

The approximately linear correlation between the germanium concentration in the silicon germanium film 710 and the thickness 950 of the layer of thermal oxide 810 has been described with reference to graph 1000 in FIG. 10 and to graph 1100 of FIG. 11. The presence of germanium in the underlying silicon germanium film 710 increases the rate at which the layer of thermal oxide 810 is grown. The actual mechanism by which the germanium concentration increases the rate at which the layer of thermal oxide 810 is grown (1) may be due to a real change in the thickness of the layer of thermal oxide 810, or (2) may be due to a change in refractive index of the layer of thermal oxide 810, or (3)

may be due to the effect of optical changes in the silicon germanium film 710 under the layer of thermal oxide 810.

Figure 13:
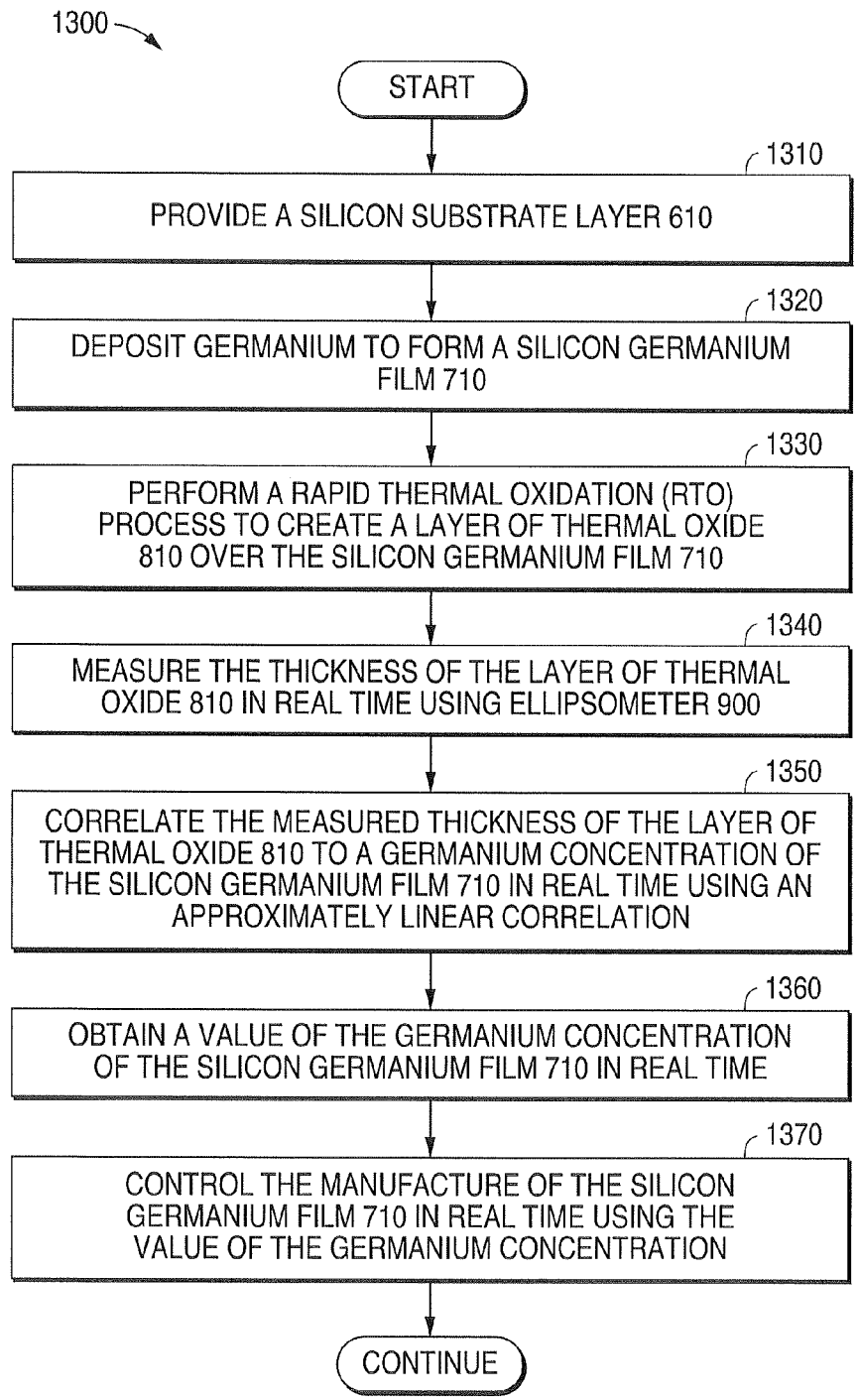
FIG. 13 illustrates a flow chart showing the steps of an advantageous embodiment of the method of the present invention.

FIG. 13 illustrates a flow chart 1300 showing the steps of an advantageous embodiment of the method of the present invention. The method of the present invention begins by providing silicon substrate layer 610 (step 1310). Then germanium is deposited to form a silicon germanium film 710 (step 1320). A rapid thermal oxidation (RTO) procedure is then performed to create a layer of thermal oxide 810 over the silicon germanium film 710 (step 1330). Then the thickness of the layer of thermal oxide 810 is measured in real time using ellipsometer 900 (step 1340).

Then the measured thickness of the layer of thermal oxide 810 is correlated in real time to a germanium concentration of the silicon germanium film 710 using an approximately linear correlation (step 1350). In this manner a value of the germanium concentration in the silicon germanium film 710 is obtained in real time (step 1370). Then the manufacture of the silicon germanium film 710 is controlled in real time using the value of the germanium concentration (step 1370).

In an alternate advantageous method of the present invention, the thickness 950 of the layer of thermal oxide 810 may be measured using an interferometer instead of ellipsometer 900. An interferometer may be used to measure the thickness of dielectric thin films such as silicon dioxide, silicon nitride and photoresist. The operational principles of an interferometer are well known in the art.

Typically, an interferometer diffracts lights from a halogen bulb (or a deuterium lamp) into its component wavelengths from about two hundred nanometers (200 nm) to about nine hundred nanometers (900 nm). A spectrophotometer scans the light from long wavelengths to short wavelengths and a microscope focuses the light onto the film whose thickness is to be measured. The interferometer measures the resulting reflectance versus wavelength and determines the thickness of the film from this data. A typical interferometer is able to measure film thicknesses from ten Ångstroms (10 Å) to five hundred thousand Ångstroms (500,000 Å). An interferometer uses a deuterium lamp source to measure film thicknesses that are less than one hundred Angstroms (100 Å).

Although the present invention has been described with an exemplary embodiment, various changes and modifications may be suggested to one skilled in the art. It is intended that the present invention encompass such changes and modifications as fall within the scope of the appended claims.

What is claimed is:

1. A method for manufacturing an integrated circuit device based on a germanium concentration of a silicon germanium film, said method comprising the steps of:
    performing a thermal oxidation procedure on said silicon germanium film to create a layer of thermal oxide over said silicon germanium film;
    measuring a thickness of said layer of thermal oxide;
    providing a correlation that relates a thickness of a layer of thermal oxide created over a silicon germanium film to a germanium concentration of said silicon germanium film; and
    determining said germanium concentration of said silicon germanium film by identifying a value of germanium concentration that corresponds to said measured thickness of said layer of thermal oxide in accordance with said correlation; and
    controlling manufacture of said integrated circuit device using said value of germanium concentration.

2. The method as set forth in claim 1 wherein said step of measuring a thickness of said layer of thermal oxide comprises measuring said thickness of said layer of thermal oxide in real time using one of: an interferometer, an ellipsometer, and a spectroscopic ellipsometer.

3. The method as set forth in claim 2 further comprising the step of:
    performing in real time said step of determining said germanium concentration of said silicon germanium film by identifying a germanium concentration that corresponds to said measured thickness of said layer of thermal oxide in accordance with said correlation.

4. The method as set forth in claim 2 further comprising the step of:
    measuring said thickness of said layer of thermal oxide in real time by making a plurality of thickness measurements of said thickness of said layer of thermal oxide in real time using one of: an interferometer, an ellipsometer, and a spectroscopic ellipsometer.

5. The method as set forth in claim 1 wherein said correlation that relates a thickness of a layer of thermal oxide created over a silicon germanium film to a germanium concentration of said silicon germanium film is an approximately linear correlation.

6. The method as set forth in claim 5 wherein said approximately linear correlation is described by:

$$\text{Oxide Thickness (Å)} = 45.55035 + 2.2670656 \text{ Ge \%}$$

where said term Oxide Thickness is in units of Angstroms; and
where said term Ge % represents a germanium concentration in a silicon germanium film in terms of germanium percentage.

7. The method as set forth in claim 5 wherein said approximately linear correlation is described by:

$$\text{Relative Oxidation Rate} = 0.9795774 + 0.0487541 \text{ Ge \%}$$

where said term Relative Oxidation Rate represents a ratio of a thickness of thermal oxide on a silicon germanium film to a thickness of thermal oxide on a silicon wafer without a silicon germanium film; and
where said term Ge % represents a germanium concentration in a silicon germanium film in terms of germanium percentage.

8. The method as set forth in claim 5 wherein said approximately linear correlation is described by:

$$\text{Ge \%} = -20.03043 + 20.470103 \text{ Relative Oxidation Rate}$$

where said term Relative Oxidation Rate represents a ratio of a thickness of thermal oxide on a silicon germanium film to a thickness of thermal oxide on a silicon wafer without a silicon germanium film; and
where said term Ge % represents a germanium concentration in a silicon germanium film in terms of germanium percentage.

9. A method for manufacturing an integrated circuit device based on a correlation between a germanium concentration of a silicon germanium film and a thickness of a layer of thermal oxide created over said silicon germanium film, said method comprising the steps of:
    creating a plurality of silicon germanium films in which each silicon germanium film has a different germanium concentration;
    creating a layer of thermal oxide over each of said plurality of silicon germanium films;

measuring a thickness of each of said layers of thermal oxide; and correlating said thickness of each of said layers of thermal oxide with a corresponding value of germanium concentration; and controlling manufacture of said integrated circuit device using a value of germanium concentration obtained from said correlation.

10. The method as set forth in claim 9 wherein said correlation between a germanium concentration of a silicon germanium film and a thickness of a layer of thermal oxide created over said silicon germanium film is an approximately linear correlation.

11. The method as set forth in claim 10 wherein said approximately linear correlation is described by:

Oxide Thickness (Å)=45.55035+2.2670656 Ge % where the oxide thickness is in units of Angstroms and the term Ge % represents a germanium concentration in a silicon germanium film in terms of germanium percentage.

12. The method as set forth in claim 10 wherein said approximately linear correlation is described by:

Relative Oxidation Rate=0.9795774+0.0487541 Ge % where said term Relative Oxidation Rate represents a ratio of a thickness of thermal oxide on a silicon germanium film to a thickness of thermal oxide on a silicon wafer without a silicon germanium film; and where said term Ge % represents a germanium concentration in a silicon germanium film in terms of germanium percentage.

13. The method as set forth in claim 10 wherein said approximately linear correlation is described by:

Ge %=−20.03043+20.470103 Relative Oxidation Rate where said term Relative Oxidation Rate represents a ratio of a thickness of thermal oxide on a silicon germanium film to a thickness of thermal oxide on a silicon wafer without a silicon germanium film; and where said term Ge % represents a germanium concentration in a silicon germanium film in terms of germanium percentage.

14. A method for manufacturing an integrated circuit device based on a germanium concentration of a silicon germanium film, said method comprising the steps of:

providing a silicon substrate layer;

depositing germanium on said silicon substrate layer to form a silicon germanium film;

performing a thermal oxidation procedure on said silicon germanium film to create a layer of thermal oxide over said silicon germanium film;

measuring a thickness of said layer of thermal oxide in real time;

providing a correlation that relates a thickness of a layer of thermal oxide created over a silicon germanium film to a germanium concentration of said silicon germanium film;

determining said germanium concentration of said silicon germanium film in real time by identifying a value of germanium concentration that corresponds to said measured thickness of said layer of thermal oxide in accordance with said correlation; and controlling manufacture of said integrated circuit device using said value of germanium concentration.

15. The method as set forth in claim 14 wherein said thermal oxidation procedure is one of: a rapid thermal oxidation procedure and a furnace oxidation procedure.

16. The method as set forth in claim 14 wherein said step of measuring a thickness of said layer of thermal oxide in real time comprises measuring said thickness of said layer of thermal oxide within a time period of approximately five minutes using one of: an interferometer, an ellipsometer, and a spectroscopic ellipsometer.

17. The method as set forth in claim 14 wherein said step of providing a correlation that relates a thickness of a layer of thermal oxide created over a silicon germanium film to a germanium concentration of said silicon germanium film comprises the step of:

providing an approximately linear correlation described by:

Oxide Thickness (Å)=45.55035+2.2670656 Ge % where the oxide thickness is in units of Angstroms and the term Ge % represents a germanium concentration in a silicon germanium film in terms of germanium percentage.

18. The method as set forth in claim 14 wherein said step of providing a correlation that relates a thickness of a layer of thermal oxide created over a silicon germanium film to a germanium concentration of said silicon germanium film comprises the step of:

providing an approximately linear correlation described by:

Relative Oxidation Rate=0.9795774+0.0487541 Ge % where said term Relative Oxidation Rate represents a ratio of a thickness of thermal oxide on a silicon germanium film to a thickness of thermal oxide on a silicon wafer without a silicon germanium film; and where said term Ge % represents a germanium concentration in a silicon germanium film in terms of germanium percentage.

19. The method as set forth in claim 14 wherein said step of providing a correlation that relates a thickness of a layer of thermal oxide created over a silicon germanium film to a germanium concentration of said silicon germanium film comprises the step of:

providing an approximately linear correlation described by:

Ge %=−20.03043+20.470103 Relative Oxidation Rate where said term Relative Oxidation Rate represents a ratio of a thickness of thermal oxide on a silicon germanium film to a thickness of thermal oxide on a silicon wafer without a silicon germanium film; and where said term Ge % represents a germanium concentration in a silicon germanium film in terms of germanium percentage.

20. The method as set forth in claim 14 wherein said step of depositing germanium on said silicon substrate layer to form a silicon germanium film comprises the step of:

exposing said silicon substrate layer to a gas comprising silane gas and germane gas in a hydrogen gas carrier.

* * * * *